(12) United States Patent
Primack (10) Patent No.: US 8,996,322 B2
(45) Date of Patent: Mar. 31, 2015

(54) METHOD AND SYSTEM FOR IMPROVING MLS-BASED MEASUREMENTS

(75) Inventor: Harel Primack, Rishon Le-Zion (IL)

(73) Assignee: Acousticeye Ltd, Tel-Aviv (IL)

(*) Notice: Subject to any disclaimer, the term of this patent is extended or adjusted under 35 U.S.C. 154(b) by 983 days.

(21) Appl. No.: 12/975,563

(22) Filed: Dec. 22, 2010

(65) Prior Publication Data

US 2011/0166808 A1   Jul. 7, 2011

Related U.S. Application Data (60) Provisional application No. 61/291,905, filed on Jan. 3, 2010.

(51) Int. Cl.
*G01H 7/00* (2006.01)
*G06F 19/00* (2011.01)

(52) U.S. Cl.
CPC .................................. *G01H 7/00* (2013.01)
USPC .................... 702/56; 73/627; 367/13

(58) Field of Classification Search
CPC ...................................................... G01H 1/003
USPC .................................................................. 702/56
See application file for complete search history.

(56) References Cited

U.S. PATENT DOCUMENTS

| | | | |
|---|---|---|---|
| 6,865,256 B1 * | 3/2005 | Descamps et al. | 379/1.04 |
| 2004/0004905 A1 * | 1/2004 | Lyon et al. | 367/13 |
| 2007/0034012 A1 * | 2/2007 | Amir et al. | 73/627 |
| 2008/0208505 A1 * | 8/2008 | Amir et al. | 702/103 |

* cited by examiner

*Primary Examiner* — Patrick Assouad
*Assistant Examiner* — Haidong Zhang
(74) *Attorney, Agent, or Firm* — Smith Risley Tempel Santos LLC; Gregory Scott Smith (57) ABSTRACT

A measurement systems that reduces spurious artifacts in reflected signals by generating and employing an improved maximum length sequence. Accurate acoustic measurements with both high SNR and low spurious artifacts are made possible by generating Wide MLS (WMLS) which modifies a base MLS by replacing each value with a sequence that includes the value and one or more additional values, where typically the replaced values have opposing polarities and, the additional signals have intermediate values. An exemplary intermediate values can be approximately zero value.

13 Claims, 6 Drawing Sheets

METHOD AND SYSTEM FOR IMPROVING MLS-BASED MEASUREMENTS

CROSS-REFERENCE TO RELATED APPLICATIONS

This application is a non-provisional application being filed under 35 USC 111 and 37 CFR 1.53(b) and claims the benefit under 35 USC 119(e) of the prior filing date of the U.S. Provisional Application for patent that was filed on Jan. 3, 2010 and assigned Ser. No. 61/291,905, which provisional is hereby incorporated by reference in its entirety. This application is related to U.S. Pat. No. 7,677,103 that was filed as non-provisional application for patent on Jul. 31, 2006 and assigned Ser. No. 11/495,642, which application is incorporated herein by reference in its entirety. This application is related to U.S. non-provisional application for patent filed on Jan. 23, 2008 and assigned Ser. No. 11/996,503, which application is incorporated herein by reference in its entirety.

BACKGROUND

The response to an impulse can be used to characterize systems which are Linear and Time-Invariant (LTI). Specifically, many types of acoustic measurements rely on emitting a short pulse to excite a physical system, and then recording of the ensuing reflections in order to characterize the system. One generic example is the measurement of various types of rooms (from small broadcasting studios to concert halls) where there is interest in measuring their acoustic impulse response. Another example is in the measurement of various tubular systems, where measured reflections give indications of faults in the tubes. These types of measurements are termed Acoustic Pulse Reflectometry (APR).

One of the limitations or pitfalls of APR is that often, the presence of background noise can considerably reduce the accuracy. Several variants or augmentations to standard APR methods can result in better Signal to Noise Ratio (SNR) such as: 1) repeating the process many times and averaging the results, which is time consuming; 2) using pulse compression methods, such as Maximum Length Sequences (MLS) and swept sine, which are equivalent to sending many pulses in a relatively short time interval, hence resulting in enhanced SNR.

MLS is a pulse compression method, which is used widely. An MLS signal is a form of pseudo-noise, for example—a sequence of +1 and −1 values, having a length of $(2^N-1)$, where N is an integer. To facilitate the MLS method, the response to this signal is recorded, and correlated with the original sequence. It has been shown extensively in the literature that the result of this correlation is very close to the impulse response of the system being measured. Using N=16, for example, should theoretically increase the SNR with a factor of 256 (~48 dB). However, in the real world the increase of the SNR does not reach the theoretical value.

BRIEF SUMMARY

We found that in current measurement systems, the use of MLS can cause spurious artifacts in the computed result. The spurious artifacts degrade the accuracy of the measurements.

Consequently, the accuracy obtained using MLS is constrained by the system. Therefore there is a need for a method that will reduce the spurious artifacts created in an MLS measuring system. Such a system can increase the Signal to Noise Ratio (SNR) obtained by using an improved MLS method.

Exemplary embodiments are described herein of methods and systems to obtain accurate acoustic measurements with both high SNR and low spurious artifacts. These embodiments transmit a new type of signal which is referred to herein as Wide MLS (WMLS). Such signals can be transmitted and received in many types of acoustic measurement applications, such as for the measurement of room acoustics, the measurements of musical instruments, the measurements of industrial tubing systems and more.

DETAILED DESCRIPTION OF EMBODIMENTS

The present disclosure describes various embodiments, aspects, features and elements of modified or enhanced MLS-based measuring systems and methods thereof. Various embodiments of the enhanced MLS-based system can best be illustrated in connection with their incorporation into a technology known as Acoustic Pulse Reflectometry (APR). An exemplary APR system for Non-Destructive Testing (NDT) of tubular systems has been described in detail in the patent application Ser. No. 11/996,503 and U.S. Pat. No. 7,677,103, which have been incorporated above by reference.

Figure 1:
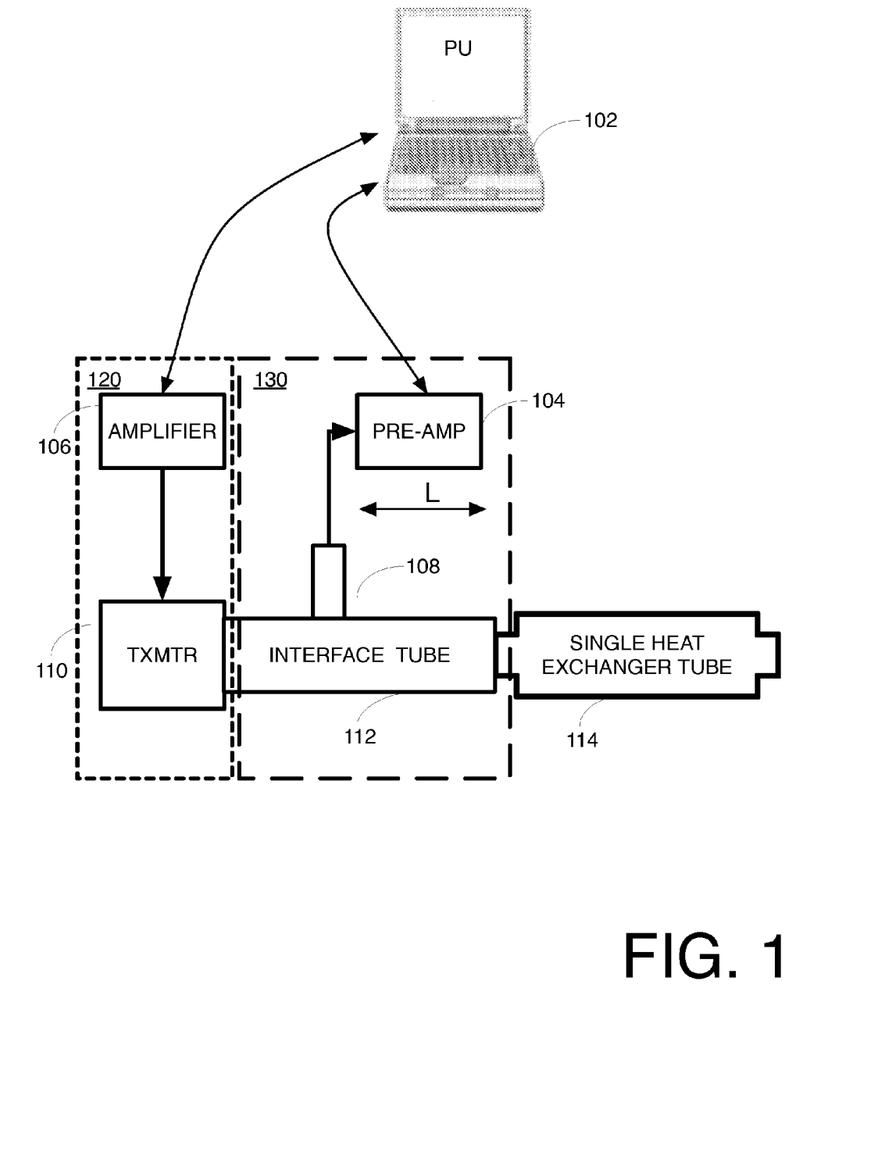
FIG. 1 is a block diagram illustrating relevant elements of an exemplary embodiment of a system for measuring and evaluating a structure using based on APR technology.

FIG. 1 is a block diagram illustrating relevant elements of an exemplary embodiment of a system for measuring and evaluating a tube based on APR technology. The illustrated hardware components of the exemplary measuring system are configured to perform Non Destructive Testing (NDT). It should be noted that the configuration illustrated in FIG. 1 is used for illustration purposes only and therefore is not shown to any particular scale and the illustrated functional boundaries are not absolutely necessary in the actual implementation of the measuring system. For example, the length of the interface tube 112 can be shorter, longer or the same as the length of the exchanger tube 114. The illustrated embodiment includes a signal injector 120 and a signal detector 130. It should be understood that the term signal and wave is used interchangeably in this description and encompasses any form of energy that can be propagated through the tube and reflected and detected. The signal injector 120 is configured to inject a signal into a medium, or interface tube 112, which acts as an interface to the target structure being tested 114. The signal detector 130 includes a sensor 108 that detects signal reflected back from the target structure 114 into the interface tube 112. The signal injector 120 and signal detector 130 may operate as a stand-alone unit, a stand-alone unit that interfaces and/or reports information to other system, a support unit that is controlled by an external processing unit 102, as well as other structures and/or configurations. For instance, in the stand-alone configuration, the processing unit may be incorporated into the signal injector and/or the signal detector 130. In such embodiments, the processing unit 102 may be as simple as a microcontroller, an ASIC or even simply analog and/or digital control circuitry. The stand-alone unit may include a user interface for initiating a test sequence or, it may simply be activated by coupling the interface tube 112 to a structure under test 114. The recorded signal may be stored in internal memory and/or information regarding the detection may be displayed to a user in a variety of manners including the use of an LCD or even simple codes displayed using lights or numbers, or audible sounds such as error codes or certain tones or buzzers may also be used.

In the illustrated embodiment, the signal injector 120 is coupled to the processing unit 102 and the structure under test 114. The signal detector 130 is coupled to the processing unit 102 and the structure under test 114.

More specifically, in the illustrated measuring system, the processing unit 102 synthesizes an acoustic pulse which is transmitted through a transmitter 110 via an amplifier 106. Thus, the processing unit 102 may include a signal generator or, a signal generator can be external to the processing unit 102, such as in the signal injector 120 or in-line between the processing unit 102 and the signal injector 120. The signal is converted into an acoustic wave by TXMTR 110, which can be a loudspeaker or similar transducer. The acoustic wave changes the pressure along the measured tube. The difference between the momentary pressure at a certain location and the static pressure at that location can be referred to as the acoustic pressure at that location. The acoustic wave first propagates down an interface tube 112, where it can be detected and/or recorded by a sensor, such as a pressure sensor 108. Sensor 108 may be a transducer, a microphone or any of a variety of other devices that can detect acoustic waves. The acoustic wave can be an acoustic wave in the form of a pulse for example, that travels down the structure 114—the target structure that is being examined. Any change in cross section of the target structure 114 will cause a reflection that will propagate back up the structure 114 and the interface tube 112, to be recorded by the pressure sensor 108, amplified by a pre-amp 104 and stored in the computer 102. The recorded reflections are analyzed in the computer 102 in order to identify the types and or severity of the faults that caused or resulted in creating the reflections. As non-limiting examples, the faults may be blockages (full or partial), pitting, erosion, cracks, kinks, bulges and holes. It will be appreciated that in some embodiments, multiple interface tubes can be utilized with each having a pressure sensor 108 but being fed by the same transmitter. In such embodiments, multiple structures can be tested at the same time or in consecutive fashion.

Figure 2:
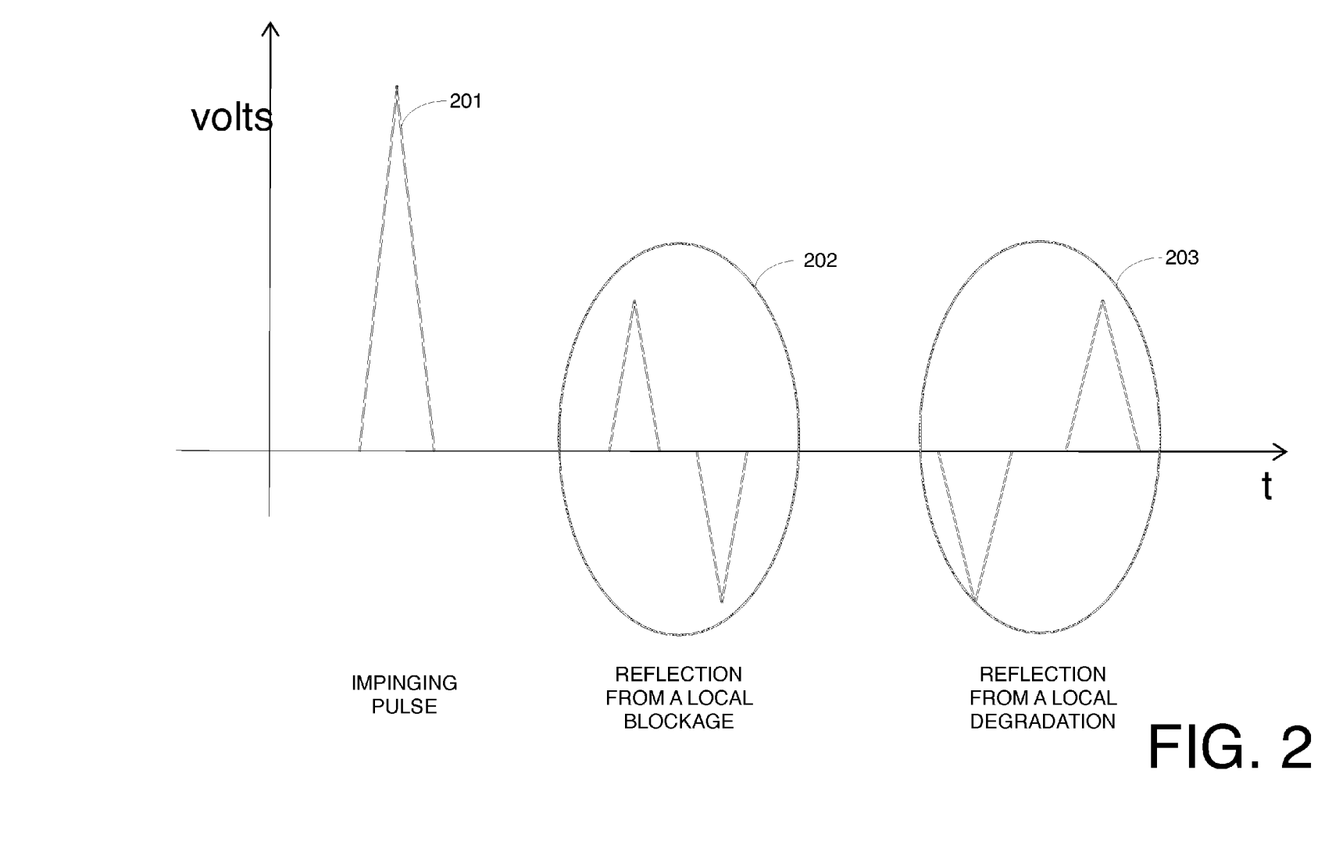
FIG. 2 is a waveform timing diagram that illustrates typical reflections from a local blockage and a local degradation in a target structure.

FIG. 2 is a waveform timing diagram that illustrates typical reflections from a local blockage and a local degradation in a target structure. The reflections illustrated in FIG. 2 are non-limiting examples of the reflections from different faults in an exemplary target structure. Supposing the impinging acoustic pulse 201 to be a sharp positive pulse as depicted in FIG. 2, the reflection from a local blockage will appear as a positive pulse (reflected from the leading edge of the blockage) followed by a negative pulse (reflected from the terminating edge of the blockage) as depicted as element 202. A reflection from wall loss such as pitting or erosion will be a negative pulse (reflected from the leading edge of the wall loss) followed by a positive one (reflected from the terminating edge of the wall loss) as depicted in element 203. More information on an exemplary NDT application and the faults is described in U.S. patent application Ser. No. 11/996,503 and U.S. Pat. No. 7,677,103, the content of which were above incorporated by reference. An exemplary NDT system can search for incidences of such reflections, locate them, classify them, quantify them and report them.

Many different excitation signals can serve as the excitation signal in the system in FIG. 1. The most straightforward is to send a short pulse. Such a pulse, however, will contain a small amount of acoustic energy. Therefore, the measured reflections will often be weak in comparison to the background noise. Repeating this procedure many times and averaging the results will improve the SNR, but this is very time consuming, since often several thousands of such repetitions are necessary. An alternative method is to send a succession of such pulses one immediately after the other, such as a stream of pulses. Using a carefully conceived or constructed series of pulses that is composed solely of values representing different binary states, known as a Maximum Length Sequence (MLS) gives the equivalent of the above repetitions in a much shorter time. The binary states may be values such as +1/−1, 1/0, on/off, high/low, true/false, etc., collectively referred to as binary values. Generally, the length of an MLS series is $2^N-1$, where N is any integer. Usage of MLS sequences relies on all of the components in the system being linear. However, in real life systems, there are distortions such as, but not limited to, nonlinear distortion caused by one or more components in the system, such as the loudspeaker for example, which may create spurious, artifactual indications in the resultant signal.

The present disclosure presents a method of using a new excitation signal based on the MLS sequence but includes more values, which is termed the Wide MLS (WMLS) signal. The MLS sequence is a series of binary values calculated by well known algorithms. The Transmitting time interval (TTI) between two consecutive binary values that are transmitted toward the loudspeaker can be defined as T.

We found that by adding one or more intermediate values, such as but not limited to 0 (zero), to a common MLS sequence of +1 and −1 the spurious artifactual indications are reduced and a better SNR is received. In some exemplary embodiments, the ±1 may have a certain amplitude, then intermediate values can be portion of this amplitude, for example ±0.2 of the amplitude. In one exemplary embodiment, in the WMLS sequence, each +1 or −1 is followed by a zero value transmitted during the following TTI. In other exemplary embodiments, each transmitting value of +1 or −1 can be followed by a series of TTIs in which more zero values are transmitted. For example, after each TTI delivering a binary value, during the next three consecutive TTIs a zero value is transmitted.

Figure 3A:
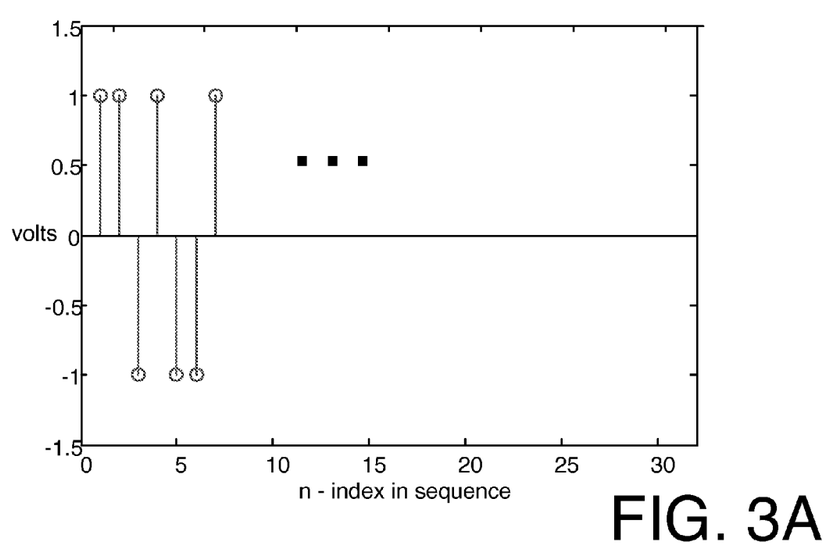
FIG. 3 shows the MLS and WLMS sequences
Figure 3B:
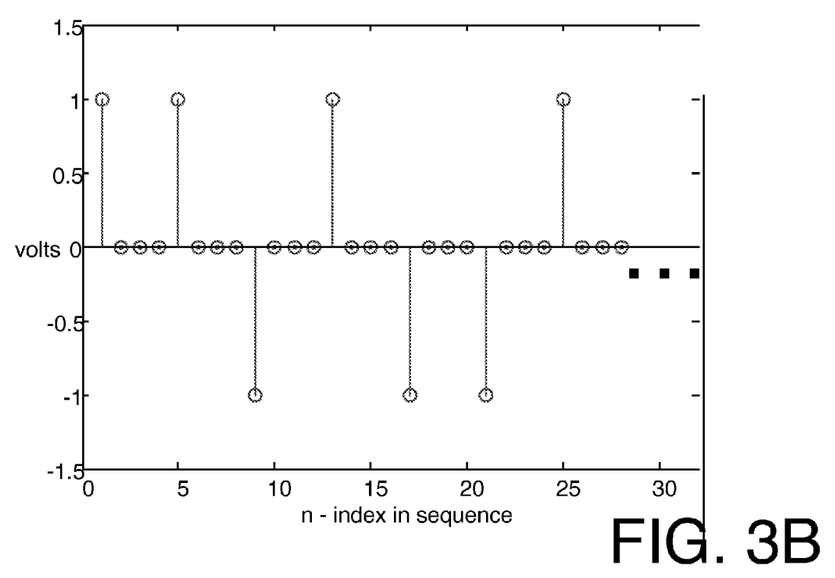

As result, the WMLS is a family of sequences, the instances of which we denote WMLS_X_Y. Here X indicates the length of the original MLS sequence, being $2^X-1$ and Y is any positive integer. In most practical cases Y can be between 4 and 16, for example. In this new sequence, every original transmitting value in the MLS sequence is replaced by a series of Y new consecutive transmitting values, the first transmitting value is taken from the MLS sequence and the rest having an intermediate value, such as but not limited to zero value. For example, if an initial MLS sequence comprises: {1; 1; −1; 1; −1; −1; 1; . . . }, then the initial part of the WMLS_X_2 sequence would be: {1; 0; 1; 0; −1; 0; 1 0; −1; 0; −1; 0; 1; 0; . . . }, and the initial part of the WMLS_X_4 sequence would be {1; 0; 0; 0; 1; 0; 0; 0; −1; 0; 0; 0; 1; 0; 0; 0; −1; 0; 0; 0; −1; 0; 0; 0; 1; 0; 0; 0; . . . }. FIG. 3A and FIG. 3B, collectively referred to as FIG. 3, are timing diagrams illustrating exemplary WMLS sequences. FIG. 3A illustrates the beginning of an above-described MLS sequence and FIG. 3B illustrates the beginning of the above-described WMLS_X_4 sequences.

Processing the signal detected at the pressure sensor 108 by the processing unit 102 is done in similar methods as for common MLS-generated signals, for example, using autocorrelation.

We found that using the WMLS sequences causes a significant decrease in the spurious artifacts caused by the system components. Because the transmission and processing time of measurements made using a WMLS sequence is greater than a regular MLS sequence, a compromise is needed. An exemplary calibration method can be used in order to define an optimal value of 'Y'. The calibration can start with 'Y' equal to zero and proceeds by incrementing the value of 'Y' by one each cycle, until reaching a value of 'Y' above which the improvements realized in the spurious artifacts can be neglected.

Figure 4:
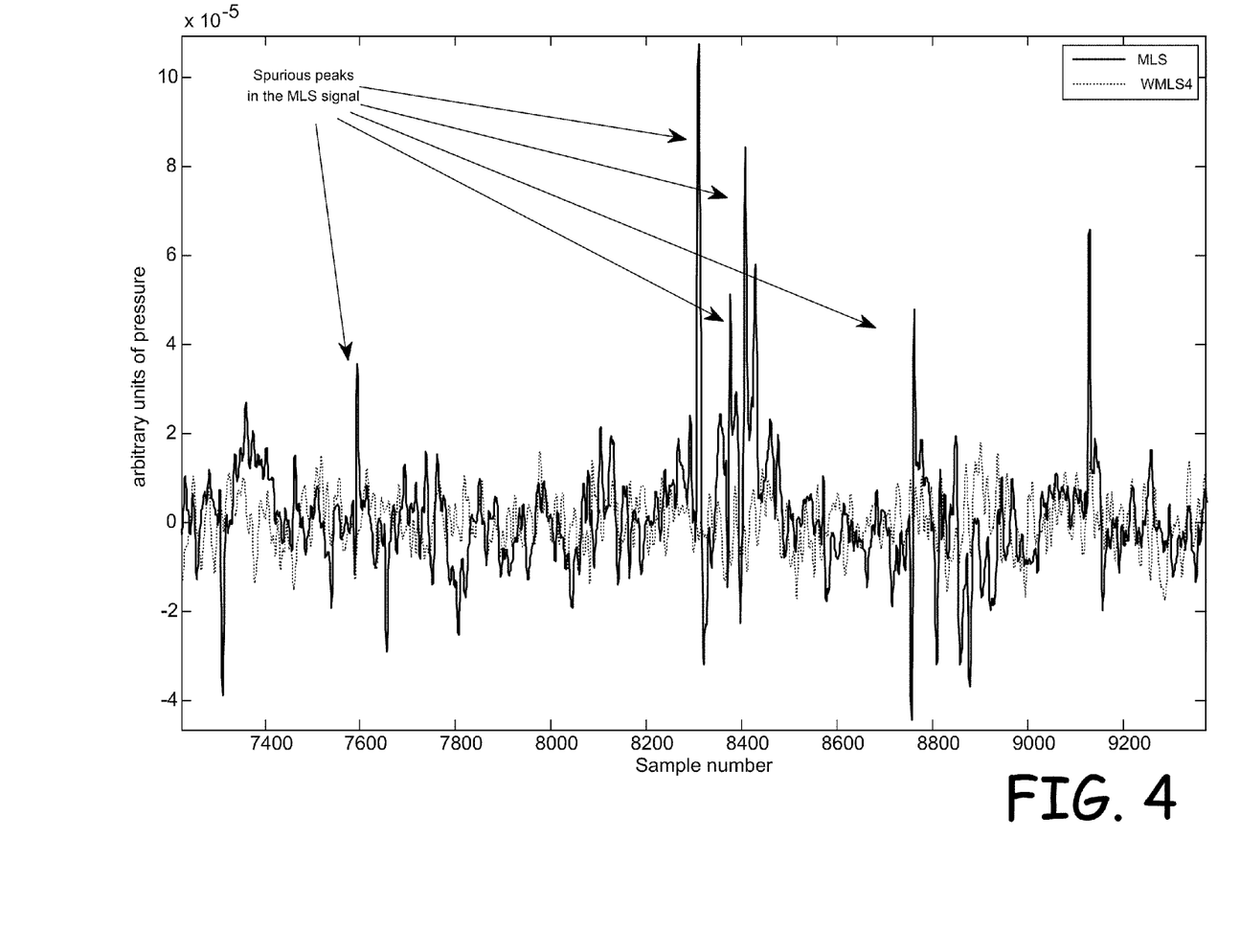
FIG. 4 shows typical measurements using MLS and WMLS signals.

FIG. 4 shows the measurements obtained with both methods MLS_16 and WMLS_16_4. The measurements were implemented on a clean new tube without any damages. Therefore, no reflections were expected. FIG. 4 illustrates one set of measurements as a solid line representing the measurements taken using the MLS_16 sequence. A second set of measurements is illustrated using a dotted line and represents the measurements taken using the WMLS_16_4 sequence. Clearly, the MLS curve includes several spikes. The spikes shown in the MLS curve were artificial and caused by the measuring system. By examining the curve for the WMLS_16_4 sequence, the artificial spikes were clearly reduced to the level of the background noise when the WMLS sequence was used.

Figure 5:
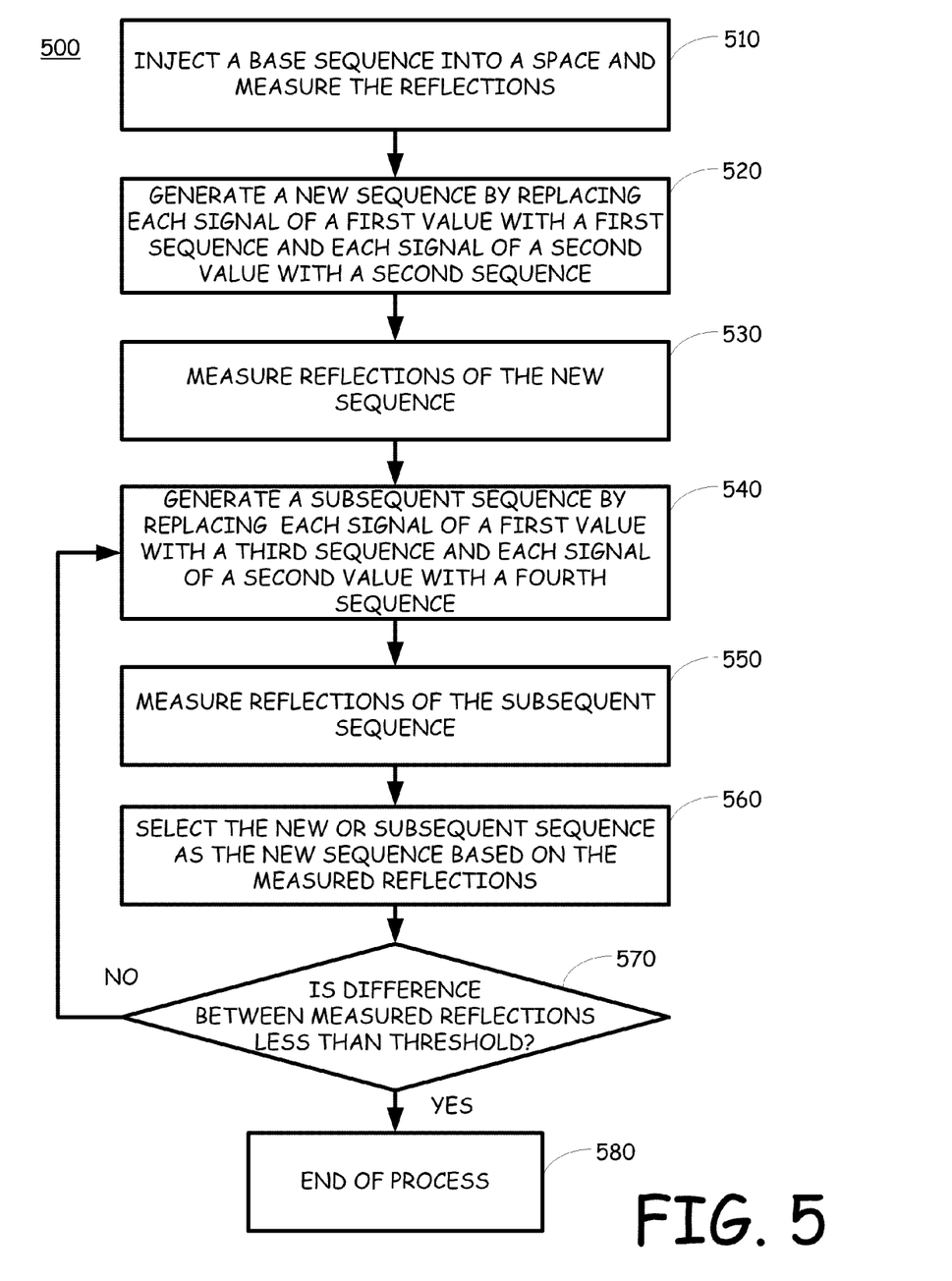
FIG. 5 is a flow diagram illustrating the actions involved in one embodiment of a process for selecting the most useful WLMS sequence

FIG. 5 is a flow diagram illustrating the actions involved in one embodiment of a process for generating a WLMS. Initially, the process 500 takes a base measurement by injecting a base sequence into a space and measuring the reflections 510. For instance, a typical MLS can be used for making such measurements. Subsequently, a new sequence can be generated, based on the MLS by replacing each signal in the sequence with a sub-sequence that includes the signal itself and one or more additional intermediate values 520. The resulting new sequence is then transmitted into the space under test and the reflections generated by the new sequence can be measured 530. A subsequent sequence can then be generated by injecting more or fewer of the additional values into each sub-sequence 540. The reflections generated as a result of transmitting the subsequent sequence into the space can also be measured 550 and then compared with the measurements of the new sequence. Whichever sequence results in reducing spurious signals the most can be set as the new sequence 560. Also, if 570 the difference in the spurious reductions between the new sequence and the subsequent sequence are negligible or, less than a threshold value, then process 500 can end 580. Otherwise, the process can return to action block 540 to generate yet another subsequent sequence. In one exemplary embodiment, the difference can be defined as the difference in the amplitude of the biggest spurious that was reflected in response to transmitting the new sequence and the amplitude of the biggest spurious that was reflected in response to transmitting the previous sequence.

Figure 6:
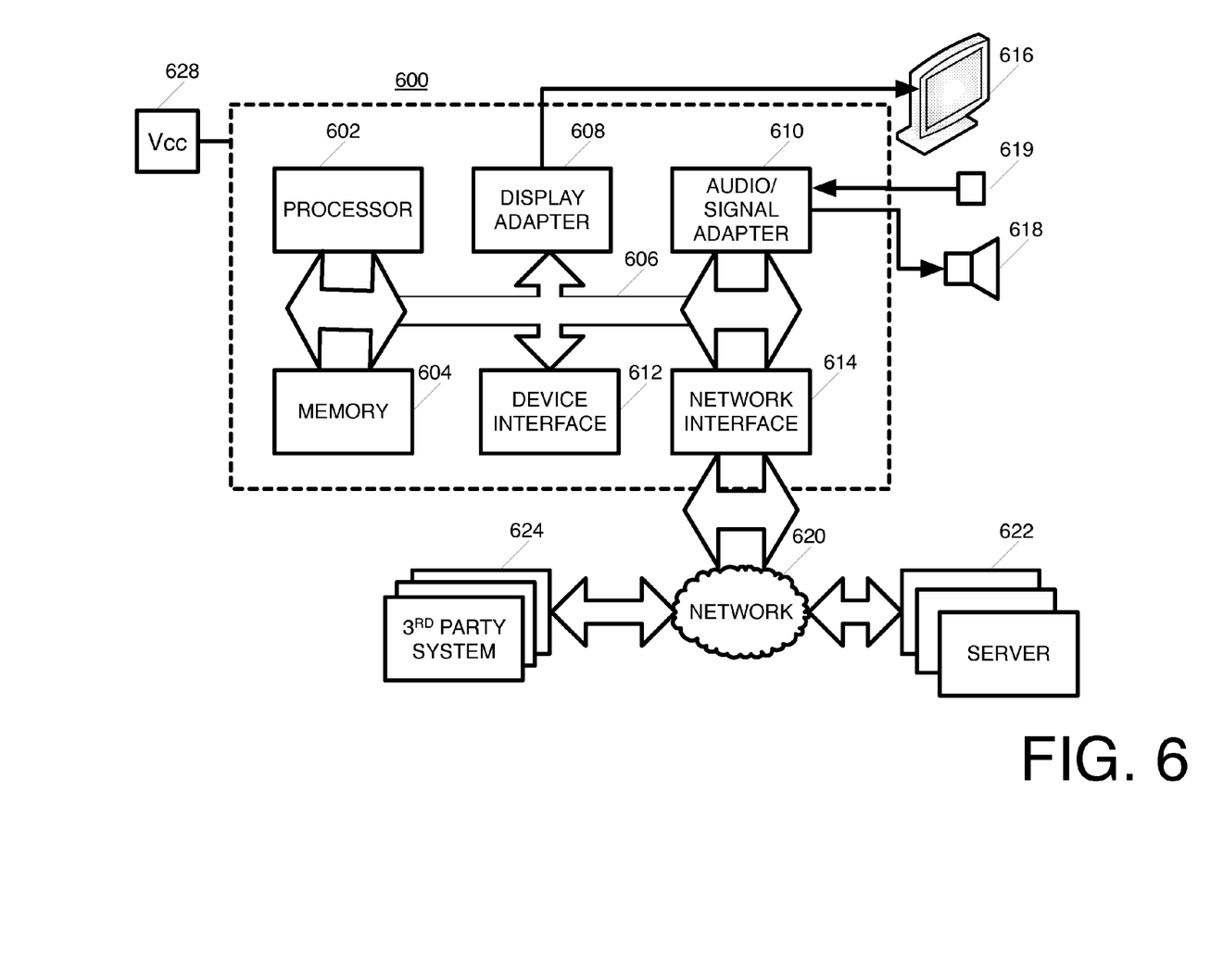
FIG. 6 is a functional block diagram of the components of an exemplary embodiment of the measuring system, as well as other embodiments thereof.

FIG. 6 is a functional block diagram of the components of an exemplary embodiment of the measuring system, as well as other embodiments thereof. It will be appreciated that not all of the components illustrated in FIG. 6 are required in all embodiments of the measuring device but, each of the components are presented and described in conjunction with FIG. 6 to provide a complete and overall understanding of the components. Further, many specific elements are not presented in FIG. 6 but rather functions and/or functional interfaces are used in a generic fashion to indicate that various embodiments may use a variety of specific components or elements. The measuring system can include a general computing platform 600 illustrated as including a processor 602 and a memory device 604 that may be integrated with each other (such as a microcontroller) or, communicatively connected over a bus or similar interface 606. The processor 602 can be a variety of processor types including microprocessors, micro-controllers, programmable arrays, custom IC's etc. and may also include single or multiple processors with or without accelerators or the like. The memory element of 604 may include a variety of structures, including but not limited to RAM, ROM, magnetic media, optical media, bubble memory, FLASH memory, EPROM, EEPROM, internal or external-associated databases, etc. The processor 604, or other components may also provide components such as a real-time clock, analog to digital converters, digital to analog converters, etc. The processor 602 also interfaces to a variety of elements including a control or device interface 612, a display adapter 608, audio/signal adapter 610 and network/device interface 614. The control or device interface 612 provides an interface to external controls or devices, such as sensor, actuators, transducers or the like. The device interface 612 may also interface to a variety of devices (not shown) such as a keyboard, a mouse, a pin pad, and audio activate device, as well as a variety of the many other available input and output devices or, another computer or processing device. The device interface may also include or incorporate devices such as sensors, controllers, converters, etc. For instance, the amplifier 106, the transmitter 110, and the preamp 104 illustrated in FIG. 1 could all be included in the device interface 612 either as internal or integrated components or, the device interface 612 may interface to the devices as external components. Alternatively the processing unit 102 illustrated in FIG. 1 could interface to the measuring elements as a stand-alone third party system through control lines, a wired network or a wireless network. The display adapter 608 can be used to drive a variety of alert elements and/or display devices, such as display devices including an LED display, LCD display, one or more LEDs or other display devices 616. The audio/signal adapter 610 interfaces to and drives another alert element 618, such as a speaker or speaker system, buzzer, bell, etc. In the various embodiments of the measuring device, the audio/signal adapter 610 could be used to generate the acoustic wave from speaker element 618 and detect the received signals at microphone 619. The amplifiers, digital-to-analog and analog-to-digital converters may be included in the processor 602, the audio/signal adapter 610 or other components within the computing platform 600 or external thereto. The network/device interface 614 can also be used to interface the computing platform 600 to other devices through a network 620. The network may be a local network, a wide area network, wireless network, a global network such as the Internet, or any of a variety of other configurations including hybrids, etc. The network/device interface 614 may be a wired interface or a wireless interface. The computing platform 600 is shown as interfacing to a server 622 and a third party system 624 through the network 620. A battery or power source 628 provides power for the computing platform 600.

In should be appreciated that various embodiments of the measuring system or method can be implemented as a system for measuring the acoustic response of a large variety of physical objects. A few non-limiting examples of such physical objects include rooms, tubes, other enclosed or partially enclosed spaces, etc. The various embodiments can be implemented through generating the WMLS sequence both in software or hardware.

Various embodiments can also be used in general fields of science and technology, where LTI systems are being analyzed, and the analysis system or method suffers from effects such as but not limited to non-linear effects that disrupt the desired SNR.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

In this application the words "unit" and "module" are used interchangeably. Anything designated as a unit or module may be a stand-alone unit or a specialized module. A unit or a module may be modular or have modular aspects allowing it to be easily removed and replaced with another similar unit or module. Each unit or module may be any one of, or any combination of, software, hardware, and/or firmware. Software can be embodied on a computer readable medium such as a read/write hard disc, CDROM, Flash memory, ROM, etc. In order to execute a certain task a software program can be loaded to an appropriate processor as needed.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A method that reduces spurious signals in an Acoustic Pulse Reflectometry "APR" measuring system used to measure impulse response of a space by transmitting a sequence of pulses into the space and measuring reflections of the transmitted sequence, the method comprising the acts of:
Selecting, by a processing unit, a sequence of signals with each signal in the sequence having a value selected from the list of values including a first value and a second value;
creating, by the processing unit, a modified sequence based on the selected sequence, wherein for each occurrence of a signal having the first value in the selected sequence, the modified sequence includes a first signal sequence and, for each occurrence of a signal having the second value in the selected sequence, the modified sequence includes a second signal sequence;
transmitting, via a transducer, the modified sequence into the space; and
measuring the reflections of the transmitted modified sequence.

2. The method of claim 1, wherein the act of creating a modified sequence further comprises the acts of:
including a first signal sequence in which the first signal sequence includes a signal having the first value, and one or more signals having a third value; and
including a second signal sequence in which the second signal sequence includes a signal having the second value, and one or more signals having a $4^{th}$ value.

3. The method of claim 2, wherein the first and second values represent positive or negative values, and the third and the $4^{th}$ values represents intermediate values between the first and second values.

4. The method of claim 3, wherein the first and second values represent high acoustic pressure at opposing polarities and the third and the $4^{th}$ values represents low acoustic pressure at opposing polarities.

5. The method of claim 1, wherein the act of creating a modified sequence further comprises the acts of:
including a first signal sequence in which the first signal sequence includes a signal having the first value, and X signals having a third value;
including a second signal sequence in which the second signal sequence includes a signal having the second value, and Y signals having a fourth value;
following the actions of transmitting the modified sequence and measuring the reflections, repeating the acts modifying the selected sequence to create an alternate modified sequence by changing the values of at least one of X and Y and repeating the actions of transmitting the alternate modified sequence and measuring the reflections;
comparing the measured reflections from the modified sequence and the alternate modified sequence and if the differences is less than a threshold value, reverting to the modified sequence for future measurements.

6. The method of claim 5, wherein the difference is defined as the difference between the amplitude of the biggest spurious that was reflected in response to transmitting the alternate modified sequence and the amplitude of the biggest spurious that was reflected in response to transmitting the modified sequence.

7. The method of claim 5, wherein if the action of comparing the measure reflections results in a difference that is not less than the threshold value, repeating the actions of modifying the selected sequence to create an alternate sequence, transmitting the alternate modified sequence, measuring the reflections comparing the measured reflections.

8. The method of claim 1, wherein the act of creating a modified sequence further comprises the acts of:
including a first signal sequence in which the first signal sequence includes a signal having the first value, and X signals having a third value;
including a second signal sequence in which the second signal sequence includes a signal having the second value, Y signals having a fourth value; and
adjusting the values of X and Y to minimize spurious signals.

9. The method of claim 1, wherein the action of adjusting the values of X and Y to minimize spurious signals further comprises the actions of:
measuring reflections caused by transmitting the selected sequence into the space;
generating a first modified sequence using a first set of values for X and Y;

measuring reflections caused by transmitting the first modified sequence into the space;

measuring reflections caused by transmitting the first modified sequence into the space;

generating a subsequent modified sequence using a second set of values for X and Y;

measuring reflections caused by transmitting the subsequent modified sequence into the space;

selecting as the modified sequence, one of the first modified sequence and the subsequent modified sequence depending on which sequence resulted in a greater reduction of spurious signals.

10. The method of claim 8, wherein the actions of generating a subsequent modified sequence using a second set of values for X and Y and measuring reflections caused by transmitting the subsequent modified sequence are repeated until the difference in the measured reflections is less than a threshold value.

11. The method of claim 1, wherein the space is a tube.

12. The method of claim 1, wherein the processing unit is at least one of a group consisting of a micro-processor, a micro-controller, a programmable array and a custom IC.

13. A method that reduces spurious signals in an Acoustic Pulse Reflectometry "APR" measuring system used to measure impulse response of a space by transmitting a sequence of pulses into the space and measuring reflections of the transmitted sequence, the method comprising the acts of:

selecting, by a processing unit, a sequence of signals with each signal in the sequence having a value selected from the list of values including a first value and a second value;

creating, by the processing unit, a modified sequence based on the selected sequence, wherein for each occurrence of a signal having the first value in the selected sequence, the modified sequence includes a first signal sequence and, for each occurrence of a signal having the second value in the selected sequence, the modified sequence includes a second signal sequence;

acoustically transmitting, via a transducer, the modified sequence into the space; and measuring the reflections of the transmitted modified sequence.

* * * * *